United States Patent [19]

Sullivan

[11] Patent Number: 5,516,909
[45] Date of Patent: May 14, 1996

[54] PROCESS FOR PRODUCING AMINE-BORANES

[75] Inventor: Jeffrey M. Sullivan, Longmont, Colo.

[73] Assignee: Boulder Scientific Company, Mead, Colo.

[21] Appl. No.: 196,254

[22] PCT Filed: Jun. 18, 1992

[86] PCT No.: PCT/US92/05141

§ 371 Date: Feb. 15, 1994

§ 102(e) Date: Feb. 15, 1994

[51] Int. Cl.$^6$ .............................. C07D 333/56; C07F 5/02
[52] U.S. Cl. .................. 546/13; 549/58; 564/8; 564/9; 564/301
[58] Field of Search ................ 546/13; 549/58; 564/8, 9, 301

[56] References Cited

U.S. PATENT DOCUMENTS

| 3,013,016 | 12/1961 | Haberlaud et al. | 260/313 |
|---|---|---|---|
| 3,127,448 | 3/1964 | Hinckley | 564/8 |
| 4,873,259 | 10/1989 | Summers et al. | 514/443 |
| 5,036,067 | 7/1991 | Girard et al. | 514/224.8 |
| 5,144,032 | 9/1992 | Arduengo | 544/229 |

OTHER PUBLICATIONS

Brown et al, JACS, vol. 64 (1942) pp. 325–329.
Taylor et al, JACS, vol. 77 (1955) pp. 1506–1507.

*Primary Examiner*—Richard L. Raymond
*Attorney, Agent, or Firm*—Edward S. Irons

[57] ABSTRACT

A method for producing amine-boranes, specifically pyridine-borane which is highly stable and of good color is described.

9 Claims, 1 Drawing Sheet

PROCESS FOR PRODUCING AMINE-BORANES

This is a 371 of PCT/US 92/05141, filed Jun. 18, 1992.

FIELD OF INVENTION

This invention relates to the production of amine-boranes. More particularly, the invention relates to the product of a stable, pure, pyridine-borane substantially free of color.

BACKGROUND OF THE INVENTION

Aromatic, aliphatic, alicyclic and aromatic heterocyclic amine-boranes are useful as reducing agents for various substrates, in reductive amination reactions, in the hydroboration of alkenes and alkynes, in procedures for the electroless plating of metals and in the synthesis of ceramic and preceramic materials.

Of particular importance in the context of this invention is the fact that pyridine-borane is a key reagent in the synthesis of zileuton [N-1(1-benzo[b] thien-2-ylethyl)-N-hydroxyurea]

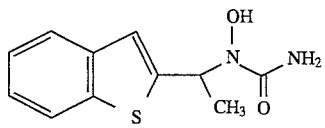

Zileuton is a 5-lipoxygenase inhibitor devoid of cyclooxygenase and 12- and 15-lipoxygenase inhibitory activity. See, e.g., *DN&P* 4(1):46 et. seq. Pyridine-borane is used in the penultimate step of zileuton synthesis as shown by the following Equation I:

EQUATION I

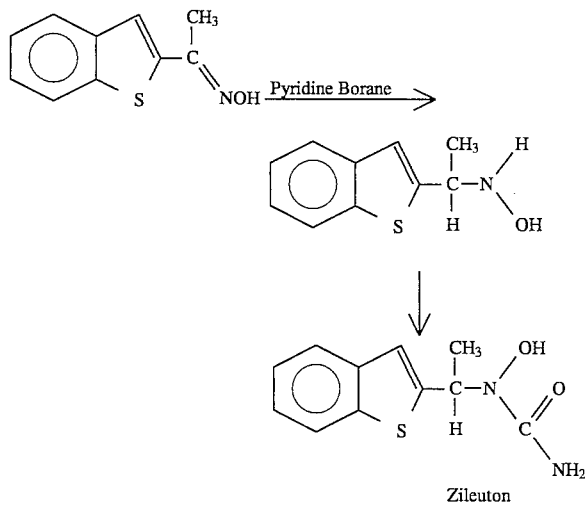

EQUATION I

The various known methods for the production of pyridine-borane are each attended by disadvantages. Pyridine-borane produced by passage of diborane through pyridine is frequently contaminated with by-products and hence unstable and of poor color. Pyridine-borane synthesis in non-aqueous systems, which require large solvent volumes with consequent low through-put also yields an unstable and impure product. Facilitation of the reactions required to produce pyridine-borane By electrolytic or mechanical agitation presents engineering difficulties and safety concerns.

The problems which attend these prior art methods create a need for a new synthesis which yields stable pyridine-borane and other amine-boranes of improved stability and color suitable for use in the synthesis of drugs such as zileuton.

SUMMARY OF THE INVENTION

This invention provides a method for the preparation of highly pure stable amine-boranes. A specific embodiment of the invention provides pure, stable pyridine-borane which is substantially free of color and hence "water white". Pursuant to the invention, pyridine is reacted with an alkali metal borohydride in a weakly acidic aqueous medium to produce a pyridine-borane containing reaction mixture. The pyridine-borane product is then stabilized with a strong base, e.g., aqueous sodium or potassium hydroxide. The pyridine-borane product is azeoptropically dried. Purity, as determined by iodometric titration, is preferably 92–96%. Yield, corrected for purity, is approximately 70–90%.

DETAILED DESCRIPTION OF THE INVENTION

Figure 1:
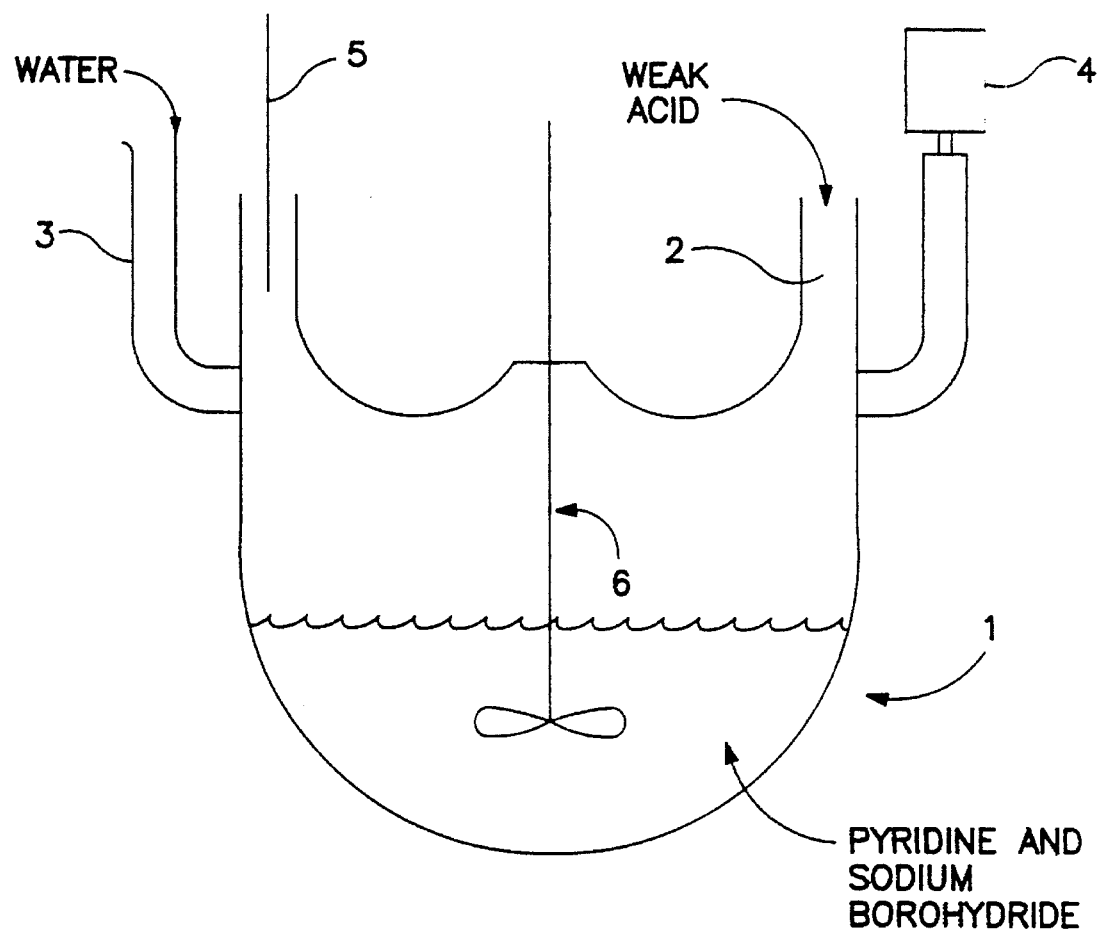
FIG. 1 is a schematic illustration of one form of apparatus which may be used to practice the invention.

The invention entails a combination of steps which yield stable pure substantially water white amine-boranes including pyridine-borane.

Pursuant to the invention, an amine such as di or trialkyl amine, preferably pyridine is reacted with an alkali metal borohydride in a weakly acidic aqueous medium. Hydrogen evolved by the reaction may be released through an oil bubbler or otherwise disposed of.

In the preferred practice of the invention, the reaction vessel is precharged with pyridine. The alkali metal borohydride is added followed by aqueous weak acid. The temperature of the reaction mixture is controlled to maximum of about 30° C. to about 35° C. Evolved hydrogen is released from the system, e.g., through an oil bubbler. The aqueous acid is preferably added over a period of about 2.5 to 3 hours.

An aqueous solution of a strong, preferably inorganic base is added to increase the pH of the reaction mixture and neutralize the excess acid. The neutralized reaction mixture separates into an upper layer containing the pyridine-borane product and a lower aqueous layer which is discarded.

The pyridine-borane product layer is preferably stabilized by addition of and agitation with an aqueous solution of a strong base. The resulting lower aqueous layer is separated and discarded. Excess pyridine is removed from the amine-borane product layer, preferably by short path distillation under reduced pressure to a final pressure of less than 5 mm Hg and a maximum pot temperature of about 50° C. to about 60° C., i.e., 50° C. to 60° C., plus or minus 5° C.

Final purity of the pyridine-borane product may be determined by iodometric titration. Final purities when so determined are usually 90 to 96%. Final yields corrected for purity are approximately 80%.

The weak acid utilized in the invention preferably has a pKa greater than 2.2. Acetic, formic, citric, and carbonic acids are appropriate. Aqueous sodium bicarbonate acid, mono and disodium phosphates may be used. Strong protic acids which have a pKa less than 2.2 in water, e.g., phosphoric, hydrochloric and sulfuric acids, can be used but provide reduced yields of lower quality pyridine-borane product.

Water and the weak acid are preferably added concurrently to the reactor containing pyridine and borohydride reactants. In the preferred practice of the invention, glacial acetic acid and water are concurrently added to the reaction mixture. The proportions of these reactants may range from about 0.5 to 2.5 but preferably is about 1:2.

Preferred alkali metal hydroxides are NaOH, KOH and LiOH, utilized in about 40% to 60% aqueous solution.

In general, the method of the invention entails the formation of an amine-borane, in particular, pyridine-borane, preferably in a weakly acid aqueous medium. The amine-borane reaction product is stabilized by agitation or the like with a strong base and then azeotropically dried. Mono, di, and trialkyl amine-boranes are produced in like manner.

EXEMPLIFICATION OF THE INVENTION

This exemplification describes the invention as applied to produce pure, stable, substantially water white, pyridine-borane in a yield, corrected for purity, of approximately 80%.

Referring to FIG. 1, the 2000 ml 3-neck flask 1 is fitted with Claisen adapters which provide two addition funnels 2 (a 125 ml funnel for glacial acetic acid) and 3 (a 250 ml funnel for water). A condensor 4 and a thermometer 5 are accommodated by the flask as shown in the Figure. A mechanical stirrer 6 is provided in the flask.

The flask 1 is charged with 145.0 g (1.83 mol) of pyridine. With cooling sodium borohydride (56.7 gr-1.50 mol) is added. The temperature of the reaction mixture is then adjusted at 20°–25° C.

Funnel 2 is charged with glacial acetic acid (95.0 g, 1.58 mol). Funnel 3 is charged with water (190 g, 10.6 mol).

Ten (10) ml of water is added to the reaction mixture from funnel 2 over a time period of 1 to 2 minutes. Within two (2) minutes simultaneous addition of acetic acid and water directly into the reaction mixture is started. The volume ratio of acetic acid:water added is initially about 1:3 and is increased gradually to 1.5 over one hour. This 1.5 ratio is maintained throughout the remaining acetic acid and water addition period of from about 2.5 to 3 hours. During the addition of acetic acid and water, the temperature of the reaction mixture rises from 20°–25° C. to 30°–35° C. Cooling is applied as necessary to maintain the temperature at about 30°–35° C. Hydrogen evolved during the reaction exits from the flask 1 by condensor 4 and is released through an oil bubbler.

About twenty minutes after completion of the water:acetic acid addition, 9.0 g of 50% aqueous NaOH is added to the reaction mixture. About ten (10) minutes thereafter, water (80 g) is added. Thereafter the contents of the flask 1 are transferred to a 1-liter separatory funnel for about 15 to 30 minutes. Thereafter the lower aqueous layer is separated and discarded.

Forty (40) grams of 50% aqueous NaOH was added with agitation to the pyridine-borane containing upper layer. The mixture forms an upper, pyridine-borane layer and a lower aqueous layer which is separated and discarded.

The pyridine-borane layer is stirred for about one hour in the presence of 4 grams of solid NaOH and then filtered.

Excess pyridine is removed by short path distillation under reduced pressure to a final pressure of less than 5 mm Hg and a maximum pot temperature of 55° C.

Final purity of the substantially water white product was determined to be 92–96% by iodometric titration. The iodometric titration was carried out by the method described in Jensen, E., et al., Anal. Chem. 24:1843 (1952).

Yield, corrected for purity, was approximately 80% based on the sodium borohydride reactant.

The pyridine-borane product is used to produce zileuton pursuant to Equation I. The zileuton product is substantially free of colored contaminants.

I claim:

1. A method for producing pyridine-borane which comprises:
   (i) charging a reaction vessel with pyridine;
   (ii) adding an alkali metal borohydride to said pyridine contained in said reaction vessel;
   (iii) thereafter concurrently adding a weak acid and water to said reaction vessel in an amount and for a time sufficient to produce the pyridine-borane;
   (iv) thereafter adding aqueous alkali metal hydroxide to neutralize the reaction mixture produced by step (iii);
   (v) separating said pyridine-borane product from said reaction mixture.

2. A method as defined by claim 1 in which said alkali metal borohydride is sodium borohydride.

3. A method as defined by claim 1 further comprising as step (vi) reacting said pyridine-borane product of step (v) with

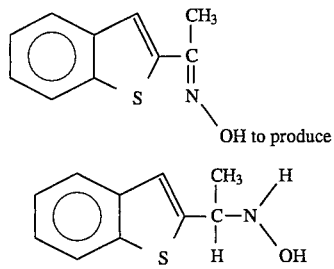

to produce

4. A method for producing an amine borane which comprises:
   (i) charging a reaction vessel with an amine;
   (ii) adding an alkali metal borohydride to said amine contained in said reaction vessel;
   (iii) thereafter concurrently adding a weak acid and water to said reaction vessel in an amount and for a time sufficient to produce the desired amine borane;
   (iv) thereafter adding aqueous alkali metal hydroxide to the reaction mixture produced by step (iii);
   (v) adding water to the product of step (iv) to provide an amine borane containing an upper layer and an aqueous lower layer; and
   (vi) separating said amine borane containing upper layer.

5. The method of claim 4 in which unreacted amine, if present, in said amine borane containing upper layer in step (v) is removed.

6. A method as defined by claim 4 in which said amine is a mono, di, or trialkyl amine and said aqueous metal hydroxide is NaOH, KOH or LiOH.

7. A method for producing pyridine-borane which comprises:
   (i) charging a reaction vessel with pyridine;

(ii) adding an alkali metal borohydride to said pyridine contained in said reaction vessel;

(iii) thereafter concurrently adding a weak acid and water to said reaction vessel in an amount and for a time sufficient to produce the pyridine-borane;

(iv) thereafter adding aqueous alkali metal hydroxide to cause the reaction mixture produced by step (iii) to form an upper pyridine-borane containing layer and a lower aqueous layer;

(v) separating said upper pyridine-borane containing layer and agitating said separated upper layer with a solid alkali metal hydroxide;

(vi) thereafter removing unreacted pyridine from said upper layer; and (vii) recovering a substantially water white pyridine-borane product having a purity of 92% to 96% as determined by iodometric titration said product being recovered in approximately 80% yield, corrected for purity, based on said alkali metal borohydride added in step (ii).

8. A method as defined by claim 7 in which said alkali metal borohydride is sodium borohydride, said weak acid is acetic acid, and said alkali metal hydroxide is sodium hydroxide.

9. Substantially water white pyridine-borane having a purity of 92% to 96% as determined by iodometric titration and produced by the method defined by claim 7 or claim 8.

* * * * *